United States Patent [19]
Gray et al.

[11] Patent Number: 6,167,313
[45] Date of Patent: Dec. 26, 2000

[54] TARGETED HYSTERESIS HYPERTHERMIA AS A METHOD FOR TREATING DISEASED TISSUE

[75] Inventors: Bruce Nathaniel Gray, Claremont; Stephen Keith Jones, Scarborough, both of Australia

[73] Assignee: Sirtex Medical Limited, West Perth, Australia

[21] Appl. No.: 09/180,399

[22] PCT Filed: May 9, 1997

[86] PCT No.: PCT/AU97/00287

§ 371 Date: Nov. 9, 1998

§ 102(e) Date: Nov. 9, 1998

[87] PCT Pub. No.: WO97/43005

PCT Pub. Date: Nov. 20, 1997

[30] Foreign Application Priority Data

May 10, 1996 [AU] Australia ................. PN9782

[51] Int. Cl.[7] ........................................ A61F 2/00
[52] U.S. Cl. .............. 607/103; 607/101; 600/9; 600/10; 600/12
[58] Field of Search ................... 607/100–104; 600/9–12

[56] References Cited

U.S. PATENT DOCUMENTS

| | | |
|---|---|---|
| 4,106,488 | 8/1978 | Gordon . |
| 4,303,636 | 12/1981 | Gordon . |
| 4,323,056 | 4/1982 | Borrelli et al. . |
| 4,545,368 | 10/1985 | Rand et al. . |
| 4,574,782 | 3/1986 | Borrelli et al. . |
| 4,662,359 | 5/1987 | Gordon . |
| 4,983,159 | 1/1991 | Rand . |
| 5,236,410 | 8/1993 | Granov et al. ............... 600/12 |
| 5,411,730 | 5/1995 | Kirpotin et al. . |
| 5,429,583 | 7/1995 | Paulus et al. ............... 600/2 |
| 5,468,210 | 11/1995 | Matsui et al. ............... 600/10 |

FOREIGN PATENT DOCUMENTS

| | | |
|---|---|---|
| 0 361 797 | 4/1990 | European Pat. Off. . |
| WO 94/12101 | 6/1994 | WIPO . |
| WO 95/15786 | 6/1995 | WIPO . |

OTHER PUBLICATIONS

International Search Report for PCT/AU97/00287.

Inductive heating of ferrimagnetic particles and magnetic fluids: physical evaluation of their potential for hyperthermia; Jordan et al.; Int. J. Hyperthermia, 1993, vol. 9, No. 1, pp. 51–68.

Evaluation of ferromagnetic materials for low–frequency hysteresis heating of tumours; Jones et al.; Phys. Med. Biol., 1992, vol. 37, No. 1, pp. 293–299.

Targeted Hyperthermia using Dextran Magnetic Complex: A New Treatment Modality for Liver Tumors; Mitsumori et al.; Hepato–Gastroenterology, 1996, vol. 43, Iss 12, pp. 1431–1437.

Intrecellular Hyperthermia for Cancer Using Magnetic Cationic Liposomes: In vitro Study; Shinkai et al.; Jpn. J. Cancer Res., vol. 87, pp. 1179–1183, Nov. 1996.

(List continued on next page.)

*Primary Examiner*—Linda C. M. Dvorak
*Assistant Examiner*—David M. Ruddy
*Attorney, Agent, or Firm*—Merchant & Gould, P.C.

[57] ABSTRACT

A method for site specific treatment of diseased tissue in a patient, comprising the steps of: (i) selecting at least a magnetic material which has a magnetic heating efficiency of at least about $4.5 \times 10^{-8}$ J.m./A.g, when magnetic field conditions are equal to or less than about $7.5 \times 10^7$ A/s; (ii) delivering the magnetic material to diseased tissue in a patient; and (iii) exposing the magnetic material in the patient to a linear alternating magnetic field with a frequency of greater than about 10 kHz and a field strength such that the product of field strength, frequency and the radius of the exposed region is less than about $7.5 \times 10^7$ A/s to generate hysteresis heat in the diseased tissue.

45 Claims, 6 Drawing Sheets

OTHER PUBLICATIONS

Gilchrist et al., Selective Inductive Heating of Lymph Nodes, Annals of Surgery, Oct. 1957, vol. 146, No. 4, pp. 596–606.

Rand et al., Selective Radiofrequency Heating of Ferrosilicone Occluded Tissue: A Preliminary Report, Bull. Los Angeles Neurol. Soc. 41(4) pp. 154–159, 1976.

Mosso et al., Ferromagnetic Silicone Vascular Occulusion: A Technic for Selective Infarction of Tumors and Organs, Ann. Of Surgery, Nov. 1972, pp. 663–668.

Rand et al., Ferromagnetic Silicone Vascular Occulusion in a Superconducting Magnetic Field Preliminary Report, Bull. Los Angeles Neurol. Soc., 1972, 37: pp. 67–74.

Rand et al., Thermomagnetic Surgery for Cancer, Journal of Surgical Research vol. 33, No. 3, Sep. 1982, pp. 177–183.

Rand et al., Thermomagnetic Surgery for Cancer, Applied Biochemistry and Biotechnology 6, pp. 265–272, 1981.

Gordon et al., Intracellular Hyperthermia A Biophysical Approach to Cancer Treatment Via Intracellular Temperature and Biophysical Alterations, Medical Hypotheses 5: pp. 83–102, 1979.

Luderer et al, Glas–Ceramic–Mediated, Magnetic–Field–Induced Localized Hyperthermia: Response of a Murine Mammary Carcinoma, Radiation Research 94, pp. 190–198, 1983.

Borrelli et al., Hysteresis heating for the treatment of tumours, Phys. Med. Biol. 1984, vol. 29, No. 5. pp. 487–494.

Matsuki et al., Highly Quality Soft Heating Method Utilizing Temperature Dependence of Permeability and Core Loss of Low Curie Temperature Ferrite, IEEE Transactions on Magnetics, vol. MAG–21, No. 5, Sep. 1985.

Matsuki et al., An Optimum Design of a Soft Heating System for Local Hyperthermia, IEEE Transactions on Magnetics, vol. MAG–23, No. 5. Sep. 1987.

Matsuki et al., Performance of Soft Heating for Locat Hyperthermia Using Temperature Sensitive Amorphous Metal Flakes, IEEE Trancactions of Magnetics, vol. 25, No. 5, Sep. 1989.

Matsuki et al, Local Hyperthermia Based on Soft Heating Method Utilizing Temperature–Sensitive Ferrite Rod, IEEE Transactions on Magnetics, vol. 26, No. 5, Sep. 1990.

Yanada et al., Evaluation of Performance of Soft Heating Element for Local Hyperthermia, IEEE Translation Journal of Magnetics in Japan, vol. 6, No. 7, Jul. 1991.

Sato et al., Ferromagnetic Amorphous Metal Microcapsules for Intra–tissue Hyperthermia and Slow Release of Anti–Cancer Agents, Proc. 16th Annual Conference IEEE Embs.1. pp. 131–133, 1992.

Sato et al., Development of a New Device and an Exciting Coil for Interstitial hyperthermia, Proc. 16th Ann. Conf. IEEE, pp. 234–235, 1992.

Sato et al., The Devolopment of Anticancer Agent Releasing Microcapsule Made of Ferromagnetic Amorphous Flakes for Intratissue Hyperthermia, IEEE Transactions on Magnetics, vol. 29, No. 6, Nov. 1993, pp. 3325–3330.

Matsuki et al., Temperature–sensitive amorphous magnetic flakes for intratissue hyperthermia, Materials Science and Engineering, A181/A182, 1994, pp. 1366–1368.

Bartlett et al., On the use of ferromagnetic microparticles in microwave and radio frequency hyperthermia, Journal of the Institution of Electronic and Radio Engineers, vol. 58, No. 4, pp. 197–201, Jun. 1988.

Suzuki et al., Studies on Liposomal Ferromagnetic Particles and a Technique of High Frequency Inductive Heating, J. Jpn. Soc. Cancer Ther. 25(11): pp. 2649–2658, Nov. 1990.

Chan et al., Synthesis and evaluation of colloidal magnetic iron oxides for the site–specific radiofrequency–induced hyperthermia of cancer, Journal of Magnetism and Magnetic Materials 122, 1993, pp. 374–378.

Jordan et al. , Inductive heating of ferrimagnetic particles and magnetic fluids: physical evaluation of their potential for hyperthermia, Int. J. Hypertermia, 1993, vol. 9, No. 1, pp. 51–68.

Jordan et al., Cellular uptake of magnetic fluid particles and their effects on human adenocarcinoma cells exposed to AC magnetic fields in vitro, Int. J. Hyperthermia, 1996, vol. 12, No. 6, pp. 705–722.

Mitsumori, Development of intra–arterial hyperthermia using a dextran–magnetic complex, Int. J. Hyperthermia, 1994, vol. 10, No. 6, pp. 785–793.

Mitsumori et al., Targeted Hyperthermia using Dextran Magnetite Complex: A New Treatment Modality for Liver Tumors, Hepato–Gastroenterology 43, 1996, pp. 1431–1437.

Shinkai et al., Antibody–conjugated magnetoliposomes for targeting cancer cells and their application in hyperthermia, Biotechnol. Appl. Biochem. 21, 1994, pp. 125–137.

Suzuki et al., Preparation and characteristics of magnetite–labelled antibody with the use of poly(ethylene glycol) derivatives, Biotechnol. Appl. Biochem. 21, pp. 335–345, 1995.

Shinkai et al., Intracellular Hyperthermia for Cancer Using Magnetite Cationic Liposomes: In vitro Study, Jpn. J. Cancer Res. 87, pp. 1179–1183, Nov. 1996.

Jones et al., Evaluation of ferromagnetic materials for low–frequency hysteresis heating of tumors, Phys. Med. Biol. 1992, vol. 37, No. 1, pp. 293–299.

Jordan et al., Magnetic Fluid Hyperthermia (MGH), Scientific and Clinical Applications of Magnetic Carriers, Plenum Press, New York, 1997, pp. 569–595.

Bacri et al., Use of Magnetic Nanoparticles for Thermolysis of Cells in a Ferrofluid, Scientific and Clinical Applications of Magnetic Carriers, Plenum Press, New York, 1997, pp. 597–606.

Chan et al., Physical Chemistry and in vivo Tissue Heating Properties of Colloidal Magnetic Iron Oxides with Increased Power Absorption Rates, Scientific and Clinical Applications of Magnetic Carriers, Plenum Press, New York, 1997, pp. 607–618.

TARGETED HYSTERESIS HYPERTHERMIA AS A METHOD FOR TREATING DISEASED TISSUE

The present invention relates to a method for treating a patient using targeted hysteresis therapy. In particular, it relates to a method of treating patients using site directed hysteresis heat loss.

Diseases of the human body such as malignant tumours are generally treated by excision, chemotherapy, radiotherapy or a combination of these approaches. Each of these is subject to limitations which effects clinical utility. Excision may not be appropriate where the disease presents as a diffuse mass or is in a surgically inoperable locality. Chemotherapeutic agents are generally non-specific, thus resulting in the death of normal and diseased cells. As with chemotherapy, radiotherapy is also non-specific and results in the death of normal tissues exposed to ionising radiation. Furthermore, some diseases such as tumours may be relatively resistant to ionizing radiation. This is a particular problem with the core of a tumour mass.

Hyperthermia has been proposed as a cancer treatment. There is a great deal of published evidence to confirm that hyperthermia is effective in treating diseases like cancerous growths. The therapeutic benefit of hyperthermia therapy is mediated through two principal mechanisms: (1) a directly tumouricidal effect on tissue by raising temperatures to greater than 42° C. resulting in irreversible damage to cancer cells; and (2) hyperthermia is known to sensitise cancer cells to the effects of radiation therapy and to certain chemotherapeutic drugs. The lack of any cumulative toxicity associated with hyperthermia therapy, in contrast to radiotherapy or chemotherapy, is further justification for seeking to develop improved systems for hyperthermia therapy.

Mammalian cells sustain hyperthermic damage in a time/temperature and cell-cycle dependent manner. This cellular response to heat is in turn modified by a variety of intra- and extra-cellular environmental factors. The intracellular factors that influence hyperthermic cell damage include intrinsic variation between different species, organs and even cell lines. The extra-cellular factors include the oxygen and nutritional status of cells, the pH of the extra-cellular mileiu, the absolute temperature rise and the hyperthermic duration.

Although there is some evidence that neoplastic cells are more sensitive than their normal tissue counterparts to the effects of hyperthermia, this is not a universal finding and several recent studies have demonstrated that tissue susceptibility to hyperthermic damage is not strongly linked to a cell's neoplastic-normal status.

A number of studies have confirmed that hyperthermia and radiotherapy are synergistic. Even small fractions of a degree of temperature variation can significantly alter the prospects of cells surviving a radiation insult.

Factors affecting the synergistic action of hyperthermia and radiotherapy include the degree of duration of hyperthermia, the sequence of hyperthermia and radiotherapy, the fractionated and total dose of radiation, the pH of the extra-cellular milieu, the oxic state and nutrient status of cells and the histological type and malignant status of the cells.

Cells in the central avascular compartment of tumours are invariably acidotic hypoxic and in a state of nutritional deprivation. All these factors appear to potentiate independently the effect of hyperthermia. By the same token, severely hypoxic cells are approximately three times more resistant to ionising radiation than oxic cells. Of major importance is the fact that although these hypoxic cells might survive the effects of radiation, hyperthermia can partly overcome this radioresistance and can potentiate radiotherapeutic killing of acidotic and hypoxic cells.

There are many problems associated with the currently available methods for inducing clinical hyperthermia in patients. Normal body tissues and organs are heat sensitive and at temperatures of greater than 42° C. many tissues will undergo irreversible damage. The current available methods of delivering clinical hyperthermia are non-specific and will heat normal tissues as well as tumour cells. Almost all heating techniques create heat generation over a broad target area with little specificity for diseased tissue, although focussing devices for both ultrasound and electromagnetic heat generation are now being developed to improve the concentration of heat generation in more defined target areas.

Several techniques are currently available for inducing clinical hyperthermia either regionally, in selected local regions of specific organs or over the whole body. Some of these techniques are discussed below.

Whole body hyperthermia may be induced by endogenous or exogenous heat sources, but is generally not tolerated above 42° C. without anaesthesia. Regional hyperthermic techniques include organ perfusion, various forms of electromagnetic radiation, or ultrasound.

Plain wave electromagnetic or ultrasound heating is limited by poor tissue penetration and a rapid decline of energy with increasing depth.

Ultrasound at frequencies of from 0.3 to 3 MHz is limited by the perturbations induced by tissue interfaces such as air, bone etc. However, improved focussing devices are being developed that may make this a more acceptable form of heating for deep tissues.

Microwave heating at frequencies between 434 and 2450 MHz has been used, although there is generally poor tissue penetration. Phase array devices are able to focus microwave energy in deep tissues, but variation in the heating effect remains a problem.

Radiofrequency waves at frequencies up to 434 MHz have been used with some success. These heating techniques include both dielectric and inductive modalities and can result in relatively even tissue heating. However, focussing for deep organ heating using inductive current remains a problem.

There are two basic requirements for such therapies to be effective. First, there is a need to localise the treatment to the target site. Second, there is a need to maximise heating within the diseased tissue while maintaining hyperthermia therapy within safe operating limits for the patient.

While considerable success has been observed in treating superficial tumours using hyperthermia therapy, there remains a need for a method of selectively targeting and treating diseased tissue in a patient. Major limitations due to insufficient penetration depth and poor focussing capabilities of externally applied microwave or ultrasound beams have grossly restricted a physicians ability to deliver an adequate heat load to deep seeded diseased without any unacceptable level of coincident damage to surrounding healthy tissue. The present invention seeks to ameliorate at least the problems associated with penetration depth and inadequate localisation of heat when using hyperthermia therapy.

SUMMARY OF THE INVENTION

The present invention provides an improved method for site specific treatment of diseased tissue in a patient, which comprises the steps of:

(i) selecting at least a magnetic material which has a magnetic heating efficiency of at least about $4.5 \times 10^{-8}$ J.m./A.g, when magnetic field conditions are equal to or less than about $7.5 \times 10^7$ A/s;

(ii) delivering the magnetic material to diseased tissue in a patient; and (iii) exposing the magnetic material in the patient to a linear alternating magnetic field with a frequency of greater than about 10 kHz and a field strength such that the product of field strength, frequency and the radius of the exposed region is less than about $7.5 \times 10^7$ A/s to generate hysteresis heat in the diseased tissue.

Preferably, steps (i) to (iii) in the method are repeated until the diseased tissue has been destroyed or treated sufficiently to ameliorate the disease.

The magnetic material employed in the method of the invention must have a magnetic heating efficiency (MHE) of greater than about $4.5 \times 10^{-8}$ J.m./A.g, when magnetic field conditions are equal to or less than about $7.5 \times 10^7$ A/s. Preferably, a magnetic material is selected which has a MHE of greater than about $7 \times 10^{-8}$ J.m./A.g, when magnetic field conditions are equal to or less than about $7.5 \times 10^7$ A/s. Most preferably, a magnetic material is selected which has a MHE of greater than about $1 \times 10^{-7}$ J.m./A.g, when magnetic field conditions are equal to or less than about $7.5 \times 10^7$ A/s.

Advantages gained by using a magnetic material with a large MHE include:

1) improved therapeutic effectiveness by virtue of the fact that higher tumour temperatures can be reached more quickly (the effectiveness of hyperthermia therapy improves markedly as temperature is increased beyond 42° C.);

2) reduced toxic side effects because:
   i. less microcapsules need to be used to achieve therapeutic heating in tumours (advantageous if the microcapsules have any intrinsic toxicity),
   ii. a lower magnetic field strength, H, can be used,
   iii. more rapid heating of the tumour may be achieved which implicates less of the healthy tumour tissue immediately surrounding the tumour (the longer time required to heat the tumour the more the immediately surrounding tissue will be heated by thermal conduction);

3) increased likelihood of successful treatment especially for tumours that would otherwise be expected to only receive a marginal benefit;

4) the techniques have a wider applicability for the treatment of different types of cancer;

5) using reduced field strengths eases engineering difficulties associated with machine design;

6) using reduced field strengths means reduced electrical power consumption and cooling requirements while running the machine.

The selection of magnetic material suitable for use in the present invention is based on the MHE of the material. MHE may be calculated using the following formula:

$$MHE = \frac{P_{hyst}}{f \cdot H} \quad (J.m/A.g) \quad (1)$$

where $P_{hyst}$ is the heating power generated by magnetic hysteresis loss effects (units W/g), H is the amplitude of the applied magnetic field (units A/m) and f is the frequency of the applied magnetic field. The major limitations to the generation of heat by magnetic hysteresis for the purposes of treating diseased tissue, arise from the effect a time varying magnetic field has on living tissue. In general these effects increase as the product of f and H increases. Hence, it is essential that $P_{hyst}$ be maximised subject to minimising the product of f and H.

Further, $P_{hyst}$ can be calculated using the following formula:

$$P_{hyst} = f \cdot W \quad (W/g) \quad (2)$$

where W is the hysteresis heat energy (units J/g) generated in the magnetic material during each cycle of the applied magnetic field and f is the frequency as before.

Combining equations (1) and (2) and eliminating f it can be seen that MHE can be calculated once H and W are known. W must be measured experimentally for each value of H. This may be achieved in the manner described herein. The MHE is then calculated from equations (1) and (2).

W can be determined using several different methods described below:

1) For magnetic hysteresis measurements a Vibrating Sample Magnetometer (VSM) is used to measure W. A known quantity (typically less than 1 g) of the magnetic powder is fixed in a non-magnetic, non-metallic VSM sample container using a non-magnetic epoxy. Samples are in an initially demagnetised state and the value of W is determined at successively higher field strengths.

2) A 50 Hz Alternating Field Magnetometer is also be used to measure W. Samples prepared as for the VSM are placed inside a small coil. This small coil is then placed between the pole pieces of a magnet that produces a magnetic field alternating at 50 Hz. The voltage induced in this coil is equal to N.dB/dt where N is the number of turns in the coil. This voltage signal is integrated, corrected for air flux and a plot of magnetisation, M, vs H is generated. This is the hysteresis loop the area of which equals W.

3) An alternative to these methods is to take a known quantity of the magnetic powder, typically 125 mg, and disperse it in 5 ml of agar gel (3% agar dissolved in warm water. The agar solidifies when cooled back to room temperature.) A temperature probe is inserted into the gel and the whole exposed to the alternating magnetic field of desired strength. From the resultant curve of Temperature vs Time it is possible to calculate W at H.

Any magnetic material which exhibits hysteresis and which has a MHE of greater than $4.5 \times 10^{-8}$ J.m./A.g, when magnetic field conditions are equal to or less than about $7.5 \times 10^7$ A/s may be used in the present invention. Preferably, the magnetic materials are ferromagnetic materials. Ferromagnetic materials may include elements such as iron, manganese, arsenic, antimony and bismuth, but are not limited to such elements. Classes of materials from which the magnetic material may be selected include $CrO_2$, gamma-ferric oxide (both cobalt treated and non-treated) and metallic iron, cobalt or nickel. Also ferrites of general form $MO.Fe_2O_3$ where M is a bivalent metal, e.g. Mg, Mn, Fe, Co, Ni, Cu, Zn, Cd or Li, cobalt treated ferrites or magnetoplumbite type oxides (M type) with general form $MO.6Fe_2O_3$ where M is a large divalent ion such as Ba, Sr or Pb are all potentially useful magnetic materials in this application. Further, superparamagnetic, single domain particles may be used as the magnetic material. Most preferably, the ferromagnetic material is selected from the class of ferromagnetic materials known as gamma-ferric oxide, ($\gamma Fe_2O_3$).

Examples of suitable ferromagnetic materials from which the magnetic materials might be selected include Co treated gamma-ferric oxide, some non cobalt treated gamma-ferric oxides, cobalt treated ferrites and chromium dioxide.

The method of the invention provides a means to increase temperature in the area of diseased tissue to above 41° C. to decrease the viability of malignant cells. A decrease in the viability of malignant cells results in either cell death or increased cell sensitivity to the effects of ionizing radiation or chemotherapeutic drugs.

The amount of hysteresis heat that is generated in a magnetic material during each cycle of an applied magnetic field is given by W. To turn hysteresis heat energy into power that is capable of heating tissue, the magnetic field must have a high frequency of alternation. During treatment, patients are placed into a machine that generates a magnetic field with strength H and frequency f. The higher the frequency the greater the rate of heating in the tissues that contain the magnetic microcapsules. However, the physiological response to high amplitude, high frequency magnetic fields limits the field amplitude and frequency that can be used in any clinical application. These limitations result from nerve muscle activation and eddy current heating which depends, inter alia, on the electrical conductivity of the tissue. Both of these are as a result of the electric fields induced in the tissue by the magnetic field. The size of these potentially deleterious induced electric fields is proportional to the square of the product of H, f and the radius of the exposed area, r, normal to the direction of the field. The product of H, f and r largely defines the magnetic field conditions. The product of H, f and r should not exceed a value of about $7.5 \times 10^7$ A/s., ie $H.f.r \leq 7.5 \times 10^7$ A/s. To illustrate this point consider the case of whole body exposure to a magnetic field applied along the body axis. In this case r is typically 0.15 m so the product of f and H should not excede about $5 \times 10^8$ A/m.s.

The magnetic material used in the invention may be delivered to the diseased tissue in a patient by any means known in the art. Suitable routes of administration might include: intratumoral, peritumoral and intravascular administrations (eg intra-arterial, intraperitoneal, subcutaneous or intrathecal injections). Preferably, the magnetic materials are delivered to the diseased tissue via the arterial or venous blood supply.

Preferably, the magnetic material is mixed in a liquid emulsion or is bound into microcapsules which may then be mixed with a suitable biocompatible medium for delivery into a patient. Most preferably the magnetic material is bound in a matrix material to form a microcapsule. Most magnetic particles themselves are, typically, too small and too dense to enable optimum delivery to the site of diseased tissue. Therefore, they are desirably encapsulated in microcapsules. Important properties of microcapsules are their density and their diameter. The density effects the efficiency of their carriage by the blood stream to the site of immobilisation in the diseased tissues vascular network while the size determines the proximity of the point of immobilisation to the diseased tissue.

Preferably, the magnetic material is bound in a matrix material which does not adversely effect the hysteresis or eddy current heating properties of the magnetic particles. The non-toxic binder or matrix material may comprise any of the suitable non-toxic materials which are well known in the microencapsulation art. Suitable materials include, for example, proteins, polymeric resins such as styrene-divinylbenzene, biopol, albumin, chitoxan etc.

In a preferred form of the invention, the microcapsules are adapted to bind or absorb or contain a cytotoxic material which is released upon heating of the microcapsule. For example the microcapsule may be composed of a porous, heat sensitive material which is non-toxic to and, preferably, inert to or compatible with animal tissue and which has embedded therewithin suitable magnetic material. The pores in the material are desirably filled with the cytotoxic compound. Upon hysteresis heating the micro-particles are capable of expanding, thereby permitting the release of the cytotoxic compound. Such particles should, however, be resistant to melting upon hysteresis heating. Thus, the use of such particles in the method of the present invention provides a single device with which combined chemotherapy and thermotherapy can be achieved to treat diseased tissue in a patient.

According to a further embodiment of the invention, an ionizing radiation source may be applied to the locus of the diseased tissue in conjunction with a magnetic field, said tissue having microcapsules as herein described included therein. The radiation source may be microcapsules which contain a radioactive compound such as Yttrium-90 or delivered from an external radiation source.

DETAILED DESCRIPTION OF THE INVENTION

Generation of heat in a range of 41° C. or higher (hyperthermia) causes irreversible damage to diseased cells. Thus, diseased tissue may be treated by elevating the diseased tissue's temperature (thermotherapy) as a result of hysteresis heat loss from suitable magnetic materials. Preferably, the heat generated by hysteresis heating is in the range of 42° C. to about 60° C.

The present invention may be used to treat any diseased tissue which may be sensitive to thermotherapy, chemotherapy or radiotherapy or a combination of thermotherapy and chemotherapy or radiotherapy. Preferably the invention is employed to treat cancerous growths or tissue which contains one or more tumours. Although the following will discuss the use of microcapsules and the method in terms of cancer/tumour treatments, it should be appreciated that applications of the method extend beyond the cancer/tumour treatments and the use only of microcapsules.

When a magnetic substance is subjected to a magnetic field with a strength that varies cyclically, some heat is generated due to magnetic hysteresis loss. The amount of heat generated per cycle depends on the hysteresis loss which varies for each different ferromagnetic material and for different magnetic field conditions. For multi-domain ferromagnetic materials the hysteresis loss is independent of particle size. Magnetic particles embedded around a tumour site and placed within an oscillating magnetic field will heat up to a temperature dependent on the magnetic properties of the material, the strength of the magnetic field, the frequency of oscillation and the cooling capacity of the blood flow in the tumour site.

Figure 1:
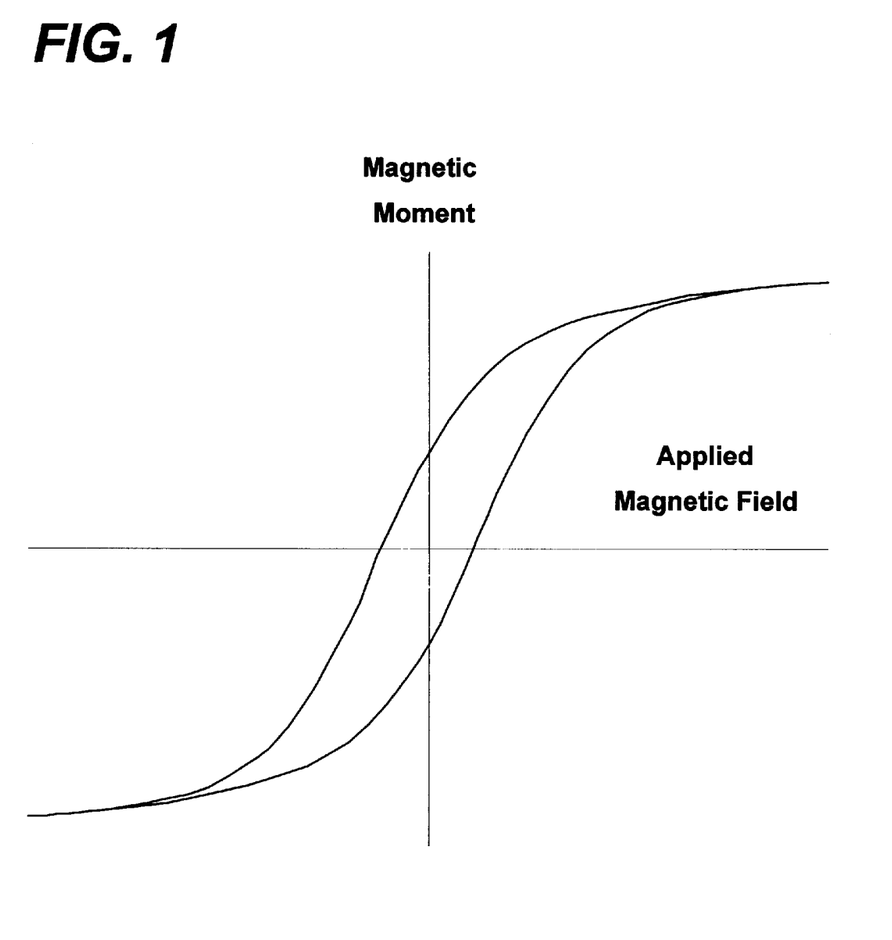
FIG. 1 shows a representative hysteresis loop illustrating how magnetisation of a magnetic sample (y-axis) varies as the applied field (x-axis) is cycled. A hysteresis loop is produced over one complete cycle. The area of this loop gives a W value.

Energy in the form of heat is produced as a result of magnetic hysteresis loss in a ferromagnetic sample whenever it is subjected to an alternating magnetic field. The amount of hysteresis energy that is generated by the magnetic material during each cycle of a magnetic field is given by W (J/g). The heating power generated by hysteresis effects is thence given by $$P_{hyst} = f \cdot W = f / p \S H dB \text{ W/g} \quad (3)$$

where f is the frequency of alternation of the applied magnetic field and p is the density of the magnetic material. The quantity §HdB is equivalent to the area of the hysteresis loop that characterises the magnetic sample under a particular set of magnetic field conditions (a typical example of a hysteresis loop is shown in FIG. (1)).

To determine the minimum amount of heat that must be generated from the magnetic microcapsules for them to be an effective therapeutic agent, $P_{tumour}$ (W/cm$^3$) needs to be ascertained. $P_{tumour}$ is given by:

$$P_{tumour} = f \cdot W_c \cdot p \cdot v \cdot n \text{ (W/cm}^3\text{)} \quad (4).$$

where f the frequency of the applied magnetic field in Hz, $W_c$ the amount of heat energy generated by hysteresis effects in the injected magnetic microcapsules each cycle of the magnetic field, units of J/g, p the density of the injected microcapsules in units of g/cm$^3$, v the volume of each microcapsules in units of cm$^3$, n the number of microcapsules per cm$^3$ of tumour tissue.

$P_{tumour}$ in essence represents the rate of tumour tissue heating. When related to the present invention $P_{tumour}$ should be large enough that it causes the temperature of the tumour tissue to increase from body temperature to a temperature that is lethal to the diseased cells over a reasonable period of time. Moreover, $P_{tumour}$ should be great enough to overcome tissue cooling influences such as blood flow and tissue thermal conductivity. Preferably, $P_{tumour}$ is greater than 60 mW/cm$^3$. Most preferably it is greater than 80 mW/cm$^3$ and desirably it is greater than 100 mW/cm$^3$.

To obtain $P_{tumour}$ values in the preferred range, suitable values need to be selected for the variables f, W, p, v and n.

Available experimental data concerning human responses to oscillating magnetic fields is limited. Such data has lead to the identification of an optimal operational frequency range between about 10 kHz and 100 MHz. For frequencies less than this there is the danger of involuntary neuromuscular activation and for higher frequencies limitations begin to arise due to reduced penetration of the electromagnetic energy into the tissue. Therefore, the frequency should be maintained within the range 10 kHz to 100 MHz. Preferably the frequency is maintained with the range 10 kHz to 500 kHz. Most preferably the frequency is maintained with the range 10 kHz to 100 kHz and desirably it would not exceed 50 kHz. For example, the frequency might be 20 kHz.

W (J/g) is an intrinsic property of the magnetic material incorporated into the microcapsules. W increases as the maximum amplitude of the applied magnetic field H, is increased. There are, however, limits to the amount that H can be increased when applying the method to patients. Such limits are also dependent on the frequency used and the area of tissue exposed to the magnetic field. The magnetic material chosen for use in the microcapsules should have a MHE of at least about $4.5 \times 10^{-8}$ J.m./A.g, when magnetic field conditions are maintained within safe operating limits for a patient. Preferably, a magnetic material is selected which has a MHE of greater than about $7 \times 10^{-8}$ J.m./A.g, when magnetic field conditions are equal to or less than about $7.5 \times 10^7$ A/s. Most preferably, a magnetic material is selected which has a MHE of greater than about $1 \times 10^{-7}$ J.m./A.g, when magnetic field conditions are equal to or less than about $7.5 \times 10^7$ A/s.

The requirements for magnetic field strength and frequency will also, depend on the properties of the microcapsules. These properties are accounted for by the parameters: p (g/cm$^3$), v (cm$^3$), and n per cm$^3$.

Microcapsules used in the method of the invention should be of a suitable size to pass through a patient's vasculature network and become dispersed and embolised within diseased tissue (with or without the assistance of vasoactive agents). The capsules used, should be capable of becoming entrapped in the precapillary and capillary network of organs, tumours or tissues without passing back into the general venous circulation. Preferably, the microcapsules should be larger than about 10 microns in diameter so that they lodge in the tumour vascular supply, and they should be smaller than about 500 micron so that they don't embolise in the blood vessels before reaching the tumour. Most preferably the microcapsules range in size between about 10 to 100 microns, with 30 to 40 microns being most desirable.

Smaller microcapsules less than 10 microns may also be used in the method if they become incorporated into tumour tissues by the process of endocytosis.

Moreover, the density of ferromagnetic material should be such, so as to allow the microcapsules to be carried by the bloodstream in a patient. The microcapsules preferably possess a density in the range 1 to 5 g/cm$^3$. Most preferably, the density should be between 1.8 to 3 g/cm$^3$. Desirably, the density is in the range 1.8 to 2.2 g/cm$^3$, for example 2 g/cm$^3$.

A number of different methods may be used to prepare the microcapsules using a diverse range of matrix materials and manufacturing techniques. In one preferred form of this invention, the microcapsules contain cobalt treated $\gamma Fe_2O_3$ particles as the ferromagnetic material, bound together using a Biopol matrix (a copolymer of (R)-3-hydroxybutyric acid and (R)-3-hydroxyvaleric acid). Using this matrix, magnetic microcapsules in a density range of 1.8–2.2 g/cm$^3$ and in a size range 20–50 microns can be obtained.

The microcapsules may be formed of bio-degradable or non-biodegradable material. Preferably, the microcapsules used in the present invention are not degradable and are permanently lodged in the tumour vascular network. Thus, they can be used repeatedly to generate localised tumour heating. By subjecting the tumour bearing organ to a magnetic field, the ferromagnetic material contained within the microcapsules will heat causing highly localised tumour heating, with preservation of the surrounding normal parenchyma.

Microcapsules may be formed by any suitable known technique (See for examples, the "Encyclopedia of Chemical Technology" KIRKO-OTTHER, Vol. 15 Wiley-Interscience). For example, ferromagnetic particles may be added to a protein solution, such as an albumin solution. The resulting protein solution should preferably then be added to an oil phase which is continually agitated thereby forming an emulsion. The proteinaceous material may then be cross-linked using heat, or chemical reagents such as glutaraldehyde to form microcapsules having ferromagnetic particles trapped therein.

In an alternative method, ferromagnetic particles may be added to a solution containing Biopol in dichloromethane. The mixture is preferably then dropped into a beaker containing poly-vinyl alcohol or the like while being mixed with a homogenising mixer. The mixture should then be left to slowly mix for a suitable period of time to allow the dichloromethane to evaporate. Microcapsules thus formed, may then be washed and size fractionated.

Following preparation of the microcapsules, the preparation may be size fractionated to select particles of a preferred size for use in the method of the invention. Preferably the preparation is also density fractionated to select for particles of a preferred density.

In one embodiment of the invention, microcapsules composed of a material which is non-toxic to and preferably inert to or compatible with an animal and which has incorporated there within at least a ferromagnetic material, are targeted (either directly or indirectly) to and delivered to diseased tissue in a patient. The microcapsules should then be subjected to a magnetic field of less than $7.5 \times 10^7$ A/s for sufficient time to treat the diseased tissue. The time required to treat such tissue will depend on the heat generated in the microcapsules which depends on magnetic field used and the properties of the microparticles employed.

A variety of administration routes are available for use in the treatment of a human or animal patient. The particular mode of administration selected will depend, of course, upon the particular condition being treated and the number of microcapsules required for therapeutic efficacy. The method of this invention, generally speaking, may be practised using any mode of administration that is medically acceptable, which is capable of selectively delivering microcapsules to diseased tissue without causing clinically adverse effects and which is capable of delivering microcapsules to diseased tissue in a patient, such that the microcapsules are distributed in a substantially even manner throughout the diseased tissue. Such modes of administration might include parenteral (eg. subcutaneous, intramuscular intraarterial and intravenous) routes.

In one embodiment of the invention microcapsules are preferably delivered by injection of a microcapsule suspension into the arterial (or portal venous) blood supply of the diseased tissue. Compositions suitable for parenteral administration conveniently comprise a sterile aqueous preparation of the capsules which is preferably isotonic with the blood of the recipient. The sterile preparation may be an injectable solution or suspension in a non-toxic parentally-acceptable diluent or solvent. Among the acceptable vehicles and solvents that may be employed are water, ringer's solution and isotonic sodium chloride solution.

The number of microcapsules per unit volume of tissue that may be used in the method will depend entirely on the amount of diseased tissue that is to be treated in a patient. Preferably, the number of microcapsule per gram of tissue is in the range of 5,000 to 300,000 (microcapsules/g). Most preferably, the range if 10,000 to 100,000, with 40,000 to 70,000 being desirable. For example, n is about 60,000 microcapsules per cubic centimeter of tumour tissue.

If, for example, the invention is used to treat a tumour or cancerous tissue, the microcapsules should be embolised into the vascular network of the tumour containing tissue so that the capsules concentrate within the tumour compartment while sparing the surrounding normal parenchyma.

The vasculature of the border area between normal tissue and the infiltrating tumour consists mainly of arterioles with adrenergic receptors, whereas vessels within the tumour lose these characteristics. Although the tumour vascular bed has little blood flow regulation, the arteriolar supply to the tumour which resides in the adjacent normal tissue is subject to normal vasomotor control. This loss of blood flow regulation in tumours underscores the principal reason why tumours cannot dissipate heat at the same rate as the ambient normal tissue when subjected to conditions of increased heat input, thus resulting in preferential heating of tumour tissue.

Progressive tumour growth results in the central region of tumours becoming relatively avascular and hypoxic. These areas do usually still contain collapsed blood vessels capable of transmitting blood flow under the influence of some vasoactive agents. The ability to lodge microparticles containing ferromagnetic material into the vascular bed of tumour tissue can be enhanced by manipulation of the blood flow of the tumour and surrounding tissues using vasoactive agents. In one embodiment of the invention the microcapsules are preferably administered to diseased tissue under the control of vasoactive drugs. Most preferably, normal parenchyma is treated with vasoconstrictive drugs to prevent microcapsules from entering that tissue.

The combined delivery of microcapsules loaded with ferromagnetic materials, and vasoactive agents such as Angiotensin II, Noradrenaline plus beta blockade, Vasopressin, Epinephrine or other vasoactive agents may open up the collapsed microcirculation in the central portions of tumours and provide access for the deliver of microcapsules into these regions. On cessation of the effect of the vasoactive agent the central portions of tumours would return to hypovascular and hypoxic state, but would be rendered susceptible to hyperthermia damage.

The phenomenon of physiologic unresponsiveness of tumour blood vessels may thus be manipulated to allow microcapsules to be selectively targeted to tumour tissue. The infusion of vasoconstrictor drugs into the arterial circulation of tumour bearing organs will cause a transient vasoconstriction of the vessels supplying the normal tissue but not those supplying the tumour. When microcapsules are introduced into the arterial circulation immediately following infusion of vasoactive drugs, the microcapsules will be preferentially directed to and trapped in the tumour vascular network and not normal tissues. The effect of the vasoactive drug will wear off within several minutes. However, by then the microcapsules will be firmly lodged in the tumour capillary network. Conversely, vasodilatory drugs may be used to selectively target radioprotectant or thermoprotectant agents to the normal non-tumour tissues.

The advantages of delivering ferromagnetic microcapsules via the vascular route compared to direct injection may be summarised as:

(i) arterial delivery of microcapsules in combination with vasoactive drug treatment allows even or substantially even distribution of the microcapsules through diseased tissue without delivery of microcapsules to normal parenchyma. In contrast, injection of microcapsules directly into diseased tissue does not result in even or substantially even microcapsule distribution. In such circumstances, microcapsules when injected into diseased tissue, focus at highest concentration, around the injection site. The density of microcapsules per unit volume of diseased tissue progressively decreases when moving away from the focal point of injection.

(ii) arterial delivery of microcapsules reduces the risk that secondary tumours will be missed, as might be the case with microcapsule delivery via injection.

(iii) arterial delivery of microcapsules avoids the need for surgical access to all tumours.

(iv) arterial delivery of microcapsules avoids the likelihood of tumour cells being spread, which might occur when a tumour is punctured by a needle.

According to a further embodiment of the invention, microcapsules loaded with ferromagnetic particles are introduced into a tumour, or a tissue containing a tumour, in conjunction with one or more vasoactive agents. A magnetic field is then applied to the locus of the tumour to induce heating either by hysteresis heating or eddy current heating of the ferromagnetic particles.

Any magnet capable of delivering desired field strengths and frequencies may be employed in the present invention. Suitable magnets include air cored coils or laminated silicon iron cored electromagnets or ferrite cored magnets. Magnets may be portable.

A number of different devices may be used to generate the appropriately conditioned time varying magnetic field.

An alternatingmagnetic field is described mathematically by:

$$H(t) = H.\text{Sin}(2\pi ft) \qquad (5)$$

where H(t) is the applied field strength at time t, H is the maximum amplitude of the applied field and f is its frequency of alternation. Any device which is capable of generating such a field may be used in the present invention.

When an alternating field is employed, the device used to generate the field, preferably uses an inductive element connected to a capacitor bank thereby forming either a series or parallel resonant circuit. The resonant circuit is preferably driven by a suitable power supply with a matching transformer. A magneto-motive force is preferably produced by a suitable inductive element such as a coil or a pair of coils. In some cases the coils may be wound onto a non-conducting high permeability core for improved operation. In one example, the coils may be fabricated from a low resistivity metal such as copper. The coils are preferably cooled by a suitable cooling means which might include, for example, circulating water or liquid nitrogen. Furthermore, the coils may be fabricated from hollow tube through which the coolant flows or they may be composed of many small diameter strands of wire, e.g. Litz wire, cooled by immersion in the coolant.

Preferably the device used in the method is capable of producing the required magnetic field conditions in a region of space large enough to accommodate a human patient. Moreover, the device is preferably capable of maximizing the MHE of the microcapsules.

Further features of the present invention are more fully described in the following Examples. It is to be understood, however, that this detailed description is included solely for the purposes of exemplifying the invention, and should not be understood in any way as a restriction on the broad description as set out above.

EXAMPLE 1

Selection Of Ferromagnetic Material

This example compares the heating efficiency of a large number of different ferromagnetic materials subjected to an alternating magnetic field.

The following ferromagnetic materials (see table 1) were obtained from industry sources:

| Ferromagnetic Material | Industry Source |
| --- | --- |
| Co-$\gamma$Fe$_2$O$_3$ (S11) | Bayer Chemicals |
| $\gamma$Fe$_2$O$_3$ (8115) | Bayer Chemicals |
| Co treated ferrite (PK5134M) | Bayer Chemicals |
| Chromium Dioxide | Dupont |
| Alnico | David Oriel Industries |
| Hexaferrite | David Oriel Industries |
| Magnequench Powder A | Delco Remy (GM) |
| Magnequench Powder B | Delco Remy (GM) |

Figure 2:
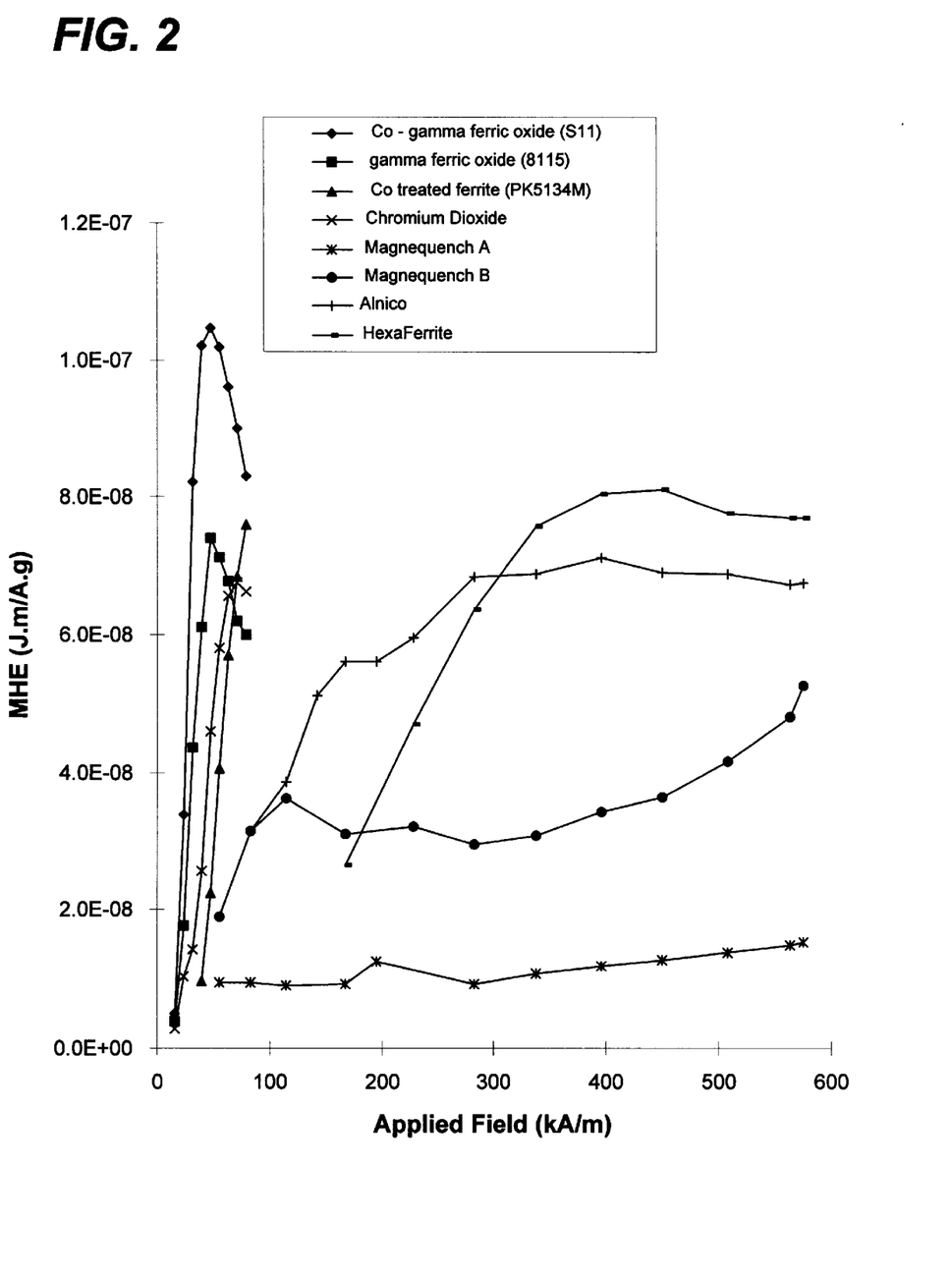
FIG. 2 shows the MHE as a function of applied magnetic field strength for a selection of magnetic materials.

The heating efficiency of these magnetic materials was examined according to the methods described earlier. The analysis involved measuring the hysteresis loop of each material in either a Vibrating Sample Magnetometer or a 50 Hz Alternating Field Magnetometer. The results of these analysis are presented graphically in FIG. 2.

Figure 3:
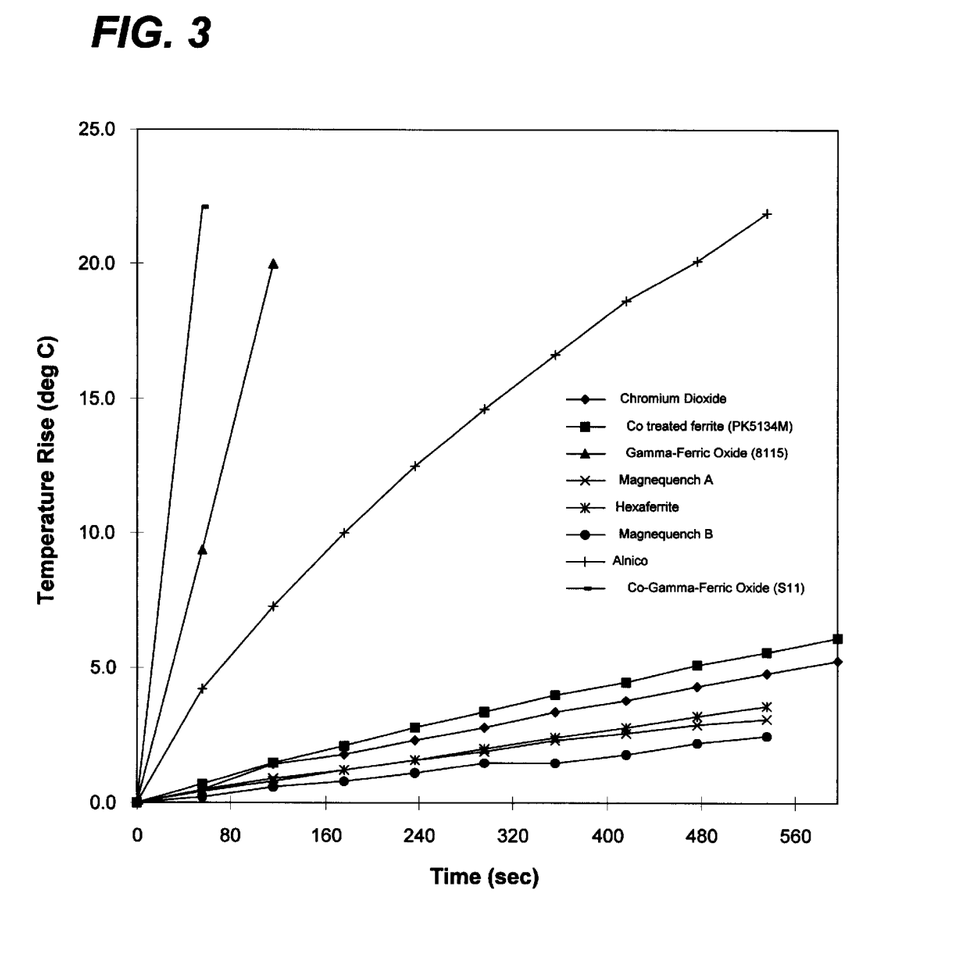
FIG. 3 shows the heating of selected magnetic materials when exposed to high frequency magnetic fields.

A direct measurement of the heat output from small samples of each of the above magnetic materials when exposed to high frequency magnetic field (53 kHz, 28 kA/m) was also made. The results of this measurement are shown graphically in FIG. 3. These results show the clearly superior heating characteristics of the $\gamma$Fe$_2$O$_3$ materials at this particular field strength (both Co treated and untreated) reflecting their higher MHE factors.

Preparation Of Ferromagnetic Microcapsules $\gamma$Fe$_2$O$_3$ particles having a maximum MHE of $1.05 \times 10^{-7}$ J.m./A.g, when the field strength was 47.1 kA/m were obtained from Bayer Chemicals. 1 g of $\gamma$Fe$_2$O$_3$ particles was thoroughly mixed with a 6 ml solution containing 15% Biopol (Fluka Chemie, Switzerland) in dichloromethane. This mixture was then dropped into a beaker containing 150 ml of 0.25% poly-vinyl alcohol (2.5 g of PVA 87–89% hydrolyzed, MW 124,000–186,000 dissolved in 1 Liter of water) while being mixed with a homogenising mixer set at 3900–4000 rpm. The mixture was then left mixing for 10 minutes after which it was left to mix very slowly for 60 minutes to allow all the dichloromethane to evaporate.

Microcapsules thus formed were washed successively through 63, 45 and 20 micron sieves. The fraction between 20 and 45 microns was kept. The capsules were then floated on diiodomethane, slightly diluted with acetone to give a specific gravity of 2.2. Any microcapsules that sink were discarded. The remainder were then washed and floated on diiodomethane diluted to a specific gravity of 1.8. The microcapsules that sink were reclaimed and washed ready for use.

Heating Of Living Tissue

This experiment shows that microcapsules when prepared by the above method can be used to heat well perfused living tissue using an amount of microcapsules that equates to a clinically relevant dose.

Figure 4:
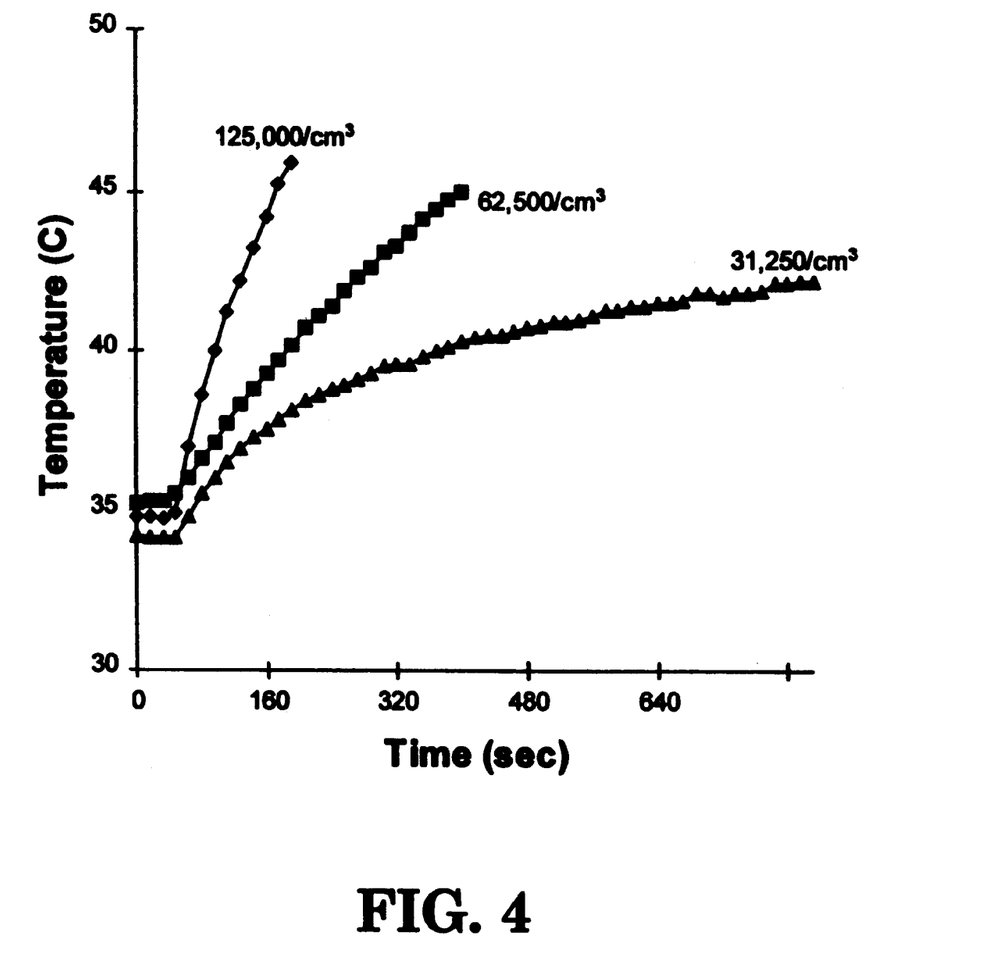
FIG. 4 illustrates the heating effectiveness of microcapsules when used to heat well perfused living tissue using an amount of microcapsules that equates to a clinically relevant dose.

Magnetic microcapsules produced according to the above method were administered to rabbit kidneys by infusion through the renal artery. Three different quantities of microcapsules were used in separate trials, 50 mg, 25 mg and 12.5 mg (corresponding to concentrations of approximately 125,000, 62,500 and 31,250 microcapsules per cubic centimeter of tissue). Thermometer probes (fluoroptic probes, Luxtron Corp). were fixed in place to measure temperatures throughout the kidney. The animals were then placed into apparatus that can produce an alternating magnetic field with strength 28 kA/m and frequency 53 kHz with radius of 0.05 m (MHE=$6.1\times10^{-8}$: Magnetic field conditions f.H.r=$7.4\times10^{7}$ A/s.). The field was then switched on and temperatures monitored for approximately 15 minutes. Typical data are shown in FIG. 4. Given that the kidney is the most highly perfused organ in the body, and hence should be the most difficult to heat, this data provides evidence that the method described is capable of heating tissue in even the most extreme conditions.

Targeted Tumour Heating

This experiment demonstrates how the above method can be used to heat liver tumours to therapeutic temperatures whilst leaving the surrounding healthy tissue unaffected.

Figure 5:
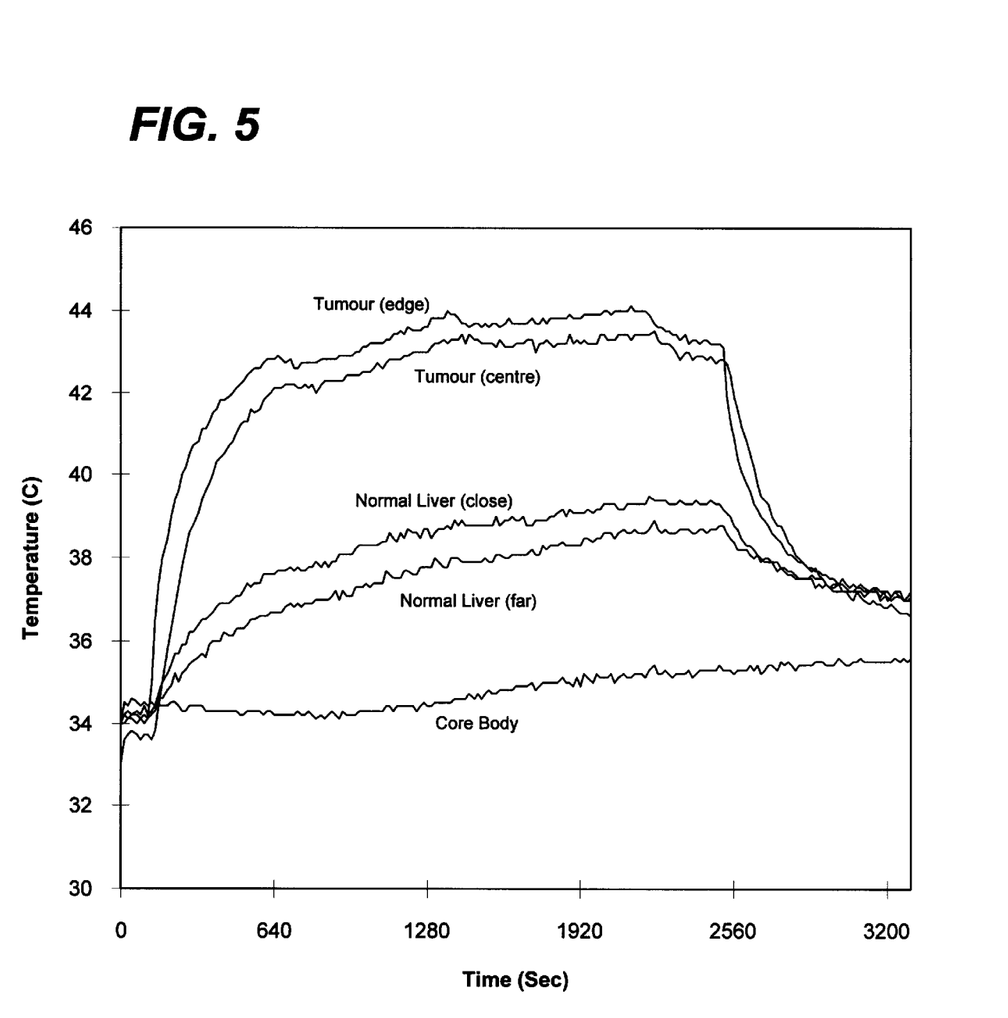
FIG. 5 illustrates the heating effectiveness of microcapsules when used to heat liver tumours to therapeutic temperatures whilst leaving the surrounding healthy tissue unaffected.

Small segments of VX2 carcinoma were implanted just under the liver surface of half lop rabbits. Once the tumours had grown to a size of approximately 1 cm$^3$, 50 mg of microcapsules, produced according to the above method, were infused using approximately 5 ml saline through a 0.8 mm O.D. catheter inserted into the cystic artery adjoining the hepatic artery feeding into the liver of the rabbits. Thermometer probes were fixed in place to measure temperatures in the necrotic core of the tumour, the growing edge of the tumour, in nearby normal liver tissue and in more distant part of the liver. The rabbits were then placed in the magnetic field apparatus as described above (f.H.r=$7.4\times10^{7}$), the field switched on and temperatures monitored. After a period of approximately 1 hour the field was switched off and temperatures were allowed to return to normal. FIG. 5 shows data from one of these procedures. The differential heating between tumour and normal tissue is clear. The tumour was heated to the therapeutic threshold temperature of 42° C. and maintained at that temperature while the normal liver temperature did not exceed 40° C.

Evaluation Of Therapeutic Effectiveness

This experiment examined the therapeutic effectiveness of the above method.

Figure 6:
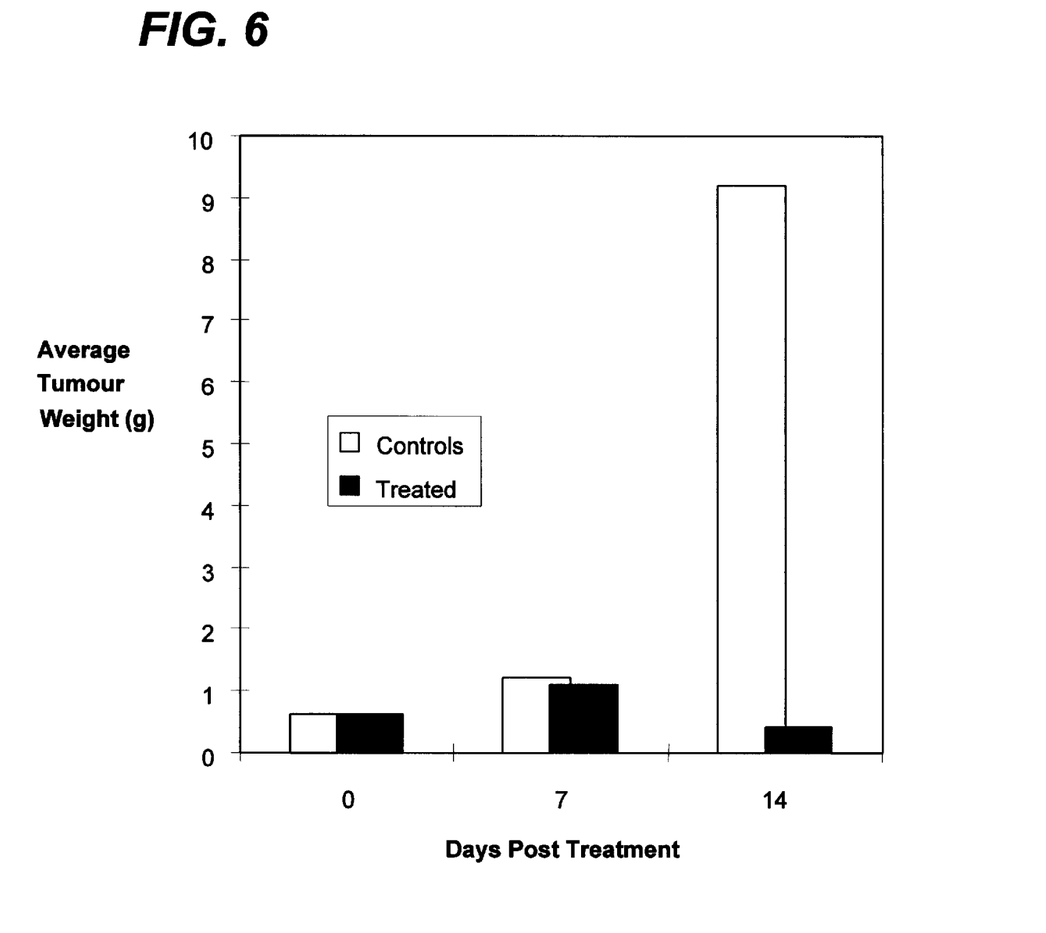
FIG. 6 illustrates the therapeutic effectiveness of the subject method in destroying diseased tissue.

The procedure described above was repeated under sterile conditions. Tumour temperatures were maintained at or above 42° C. for a period of 30 minutes. The rabbits were then revived and kept for a period of either 7 days or 14 days. At these time points rabbits were sacrificed, their livers excised and tumour weights recorded. These weights are presented in FIG. 6 along with weights for a control group that received no treatment. The results show a dramatic and clear difference in tumour weights at 14 days post treatment.

The claims defining the invention are as follows:

1. A method for site specific treatment of diseased tissue in a patient, comprising the steps of:
   (i) delivering a magnetic material which has a magnetic heating efficiency of at least about $4.5\times10^{-8}$ J.m./A.g. when magnetic field conditions are equal to or less than about $7.5\times10^{7}$ A/s to diseased tissue in a patient; and
   (ii) exposing the magnetic material in the patient to a linear alternating magnetic field with a frequency of greater than about 10 kHz and a field strength such that the product of field strength, frequency, and the radius of the exposed region is less than about $7.5\times10^{7}$ A/s to generate hysteresis heat in the diseased tissue.

2. The method of claim 1, wherein steps (i) to (ii) are repeated until the diseased tissue has at least been treated sufficiently to ameliorate the disease.

3. The method of claim 1, wherein the diseased tissue contains at least a cancerous growth or contains one or more tumours.

4. The method of claim 1, wherein the magnetic material has a magnetic heating efficiency of greater than about $7\times10^{-8}$ J.m./A.g., when magnetic field conditions are equal to or less than about $7.5\times10^{7}$ A/s.

5. The method of claim 1, wherein the magnetic material has a magnetic heating efficiency of greater than about $1\times10^{-7}$ J.m./A.g., when magnetic field conditions are equal to or less than about $7.5\times10^{7}$ A/s.

6. The method of claim 1, wherein the magnetic material comprises a ferromagnetic material which contains at least an element selected from the group consisting of iron, manganese, arsenic, antimony, and bismith.

7. The method of claim 1, wherein the magnetic material is selected from compounds within the group of $CrO_2$, metallic iron, cobalt, nickel, gamma-ferric oxide, cobalt-treated gamma-ferric oxide, ferrites of the general formula $MO.Fe_2O_3$ where M is a bivalent metal, cobalt-treated ferrites, or magnetoplumbite-type oxides (M type) with the general formula $MO.6Fe_2O_3$ where M is a large divalent ion.

8. The method of claim 7, wherein the magnetic material is a compound within the group of cobalt-treated gamma-ferric oxide compounds.

9. The method of claim 7, wherein the magnetic material is a compound within the group of un-modified gamma-ferric oxide compounds.

10. The method of claim 7, wherein the magnetic material is a compound within the group of chromium dioxide compounds.

11. The method of claim 1, wherein the magnetic material is mixed in a biocompatible liquid emulsion prior to delivery into a patient.

12. The method of claim 1, wherein the magnetic material is bound in a matrix to form microcapsules.

13. The method of claim 12, wherein the microcapsules range in size from about 10 to about 100 microns.

14. The method of claim 13, wherein the microcapsules range in size from about 20 to about 50 microns.

15. The method of claim 14, wherein the microcapsules range in size from about 30 to about 40 microns.

16. The method of claim 12, wherein the microcapsules are adapted to bind, absorb, or contain a cytotoxic material which is released upon heating of the microcapsule.

17. The method of claim 12, wherein an ionizing radiation is applied to the diseased tissue in conjunction with the magnetic field.

18. The method of claim 17, wherein the radiation is applied by microcapsules which contain a radioactive compound.

19. The method of claim 1, wherein said exposing produces a rate of tissue heating greater than 60 mW/cm$^3$.

20. The method of claim 19, wherein the rate of tissue heating is greater than 80 mW/cm$^3$.

21. The method of claim 19, wherein the rate of tissue heating is greater than 100 mW/cm$^3$.

22. The method of claim 1, wherein the linear alternating magnetic field has an operational frequency of from about 10 kHz to 100 MHz.

23. The method of claim 1, wherein the linear alternating magnetic field has an operational frequency of from about 10 kHz to 500 kHz.

24. The method of claim 1, wherein the linear alternating magnetic field has an operational frequency of from about 10 kHz to 100 kHz.

25. The method of claim 1, wherein the magnetic field has an operational frequency of 20 kHz.

26. The method of claim 12, wherein the microspheres are of a suitable size to pass through a patient's vasculature network and become dispersed and embolized within diseased tissue.

27. The method of claim 12, wherein the microcapsules range in density from 1 to 5 g/cm$^3$.

28. The method of claim 12, wherein the microcapsules range in density from 1.8 to 3 g/cm$^3$.

29. The method of claim 12, wherein the microcapsules range in density from 1.8 to 2.2 g/cm$^3$.

30. The method of claim 12, wherein the microcapsules have a density of about 2 g/cm$^3$.

31. The method of claim 1, wherein the magnetic material is bound together using a copolymer of (R)-3-hydroxybutyric acid and (R)-3-hydroxyvaleric acid.

32. The method of claim 1, wherein the magnetic material is bound together using a copolymer of (R-3-hydroxybutyric acid and (R)-3-hydroxyvaleric acid, having a density range of 1.8–2.2 g/cm$^3$ and a range in size from 20–50 microns.

33. The method of claim 3, wherein the magnetic material is delivered to the diseased tissue by any one of the administration methods selected from the group consisting of intratumoral, peritumoral, or intravascular administrations.

34. The method of claim 1, wherein the magnetic material is delivered to the diseased tissue by arterial or venous blood supply.

35. The method of claim 1, wherein the magnetic material is delivered to the diseased tissue in combination with at least a vasoactive agent.

36. A method for generating hysteresis heat in a tissue, comprising:

delivering to the tissue magnetic material having a magnetic heating efficiency of at least about $4.5 \times 10^{-8}$ J.m./A.g., when the magnetic field conditions are about $7.5 \times 10^7$ A/s or less; and exposing the tissue, containing the delivered magnetic material, to a linear alternating magnetic field with a frequency of about 10 kHz or greater and a field strength such that the product of field strength, frequency, and the radius of the exposed tissue is less than about $7.5 \times 10^7$ A/s to generate hysteresis heat in the tissue.

37. The method of claim 36, wherein the tissue contains at least a cancerous growth or contains one or more tumor.

38. The method of claim 37, wherein said delivery and exposure are repeated until said cancerous growth or tumor is reduced in size.

39. A method for the treatment of cancerous growth or tumors, comprising:

delivering to a tissue containing a cancerous growth or tumor, a magnetic material having a magnetic heating efficiency of at least about $4.5 \times 10^{-8}$ J.m./A.g., when the magnetic field conditions are about $7.5 \times 10^7$ A/s or less; and exposing the tissue, containing the delivered magnetic material, to a linear alternating magnetic field with a frequency of about 10 kHz or greater and a field strength such that the product of field strength, frequency, and the radius of the exposed tissue is less than about 7.5x10e7 A/s to generate hysteresis heat in the tissue.

40. A method for the heat treatment of a target tissue in a patient, comprising the steps of:

administering to the patient's tissue magnetic material having a magnetic heating efficiency of at least about $4.5 \times 10^{-8}$ J.m./A.g., when the magnetic field conditions are about $7.5 \times 10^7$ A/s or less; and selectively exposing the tissue to a linear alternating magnetic field with a frequency of about 10 kHz or greater and a field strength such that the product of field strength, frequency, and the radius of the exposed tissue is less than about 7.5x10e7 A/s to generate hysteresis heat in the tissue.

41. The method of claim 40, wherein said administering comprises injecting microcapsules comprising the magnetic material.

42. The method of claim 40, wherein said microcapsules further comprise a cytotoxic agent.

43. The method of claim 40, further comprising the step of:

exposing the tissue to ionizing radiation.

44. The method of claim 43, wherein said exposure is from an external radiation source.

45. The method of claim 41, wherein said microcapsules further comprise a radioactive compound.

* * * * *

UNITED STATES PATENT AND TRADEMARK OFFICE
CERTIFICATE OF CORRECTION

PATENT NO. : 6,167,313
DATED : December 26, 2000
INVENTOR(S) : Gray et al.

It is certified that error appears in the above-identified patent and that said Letters Patent is hereby corrected as shown below:

Column 15,
Line 13, "(R-3-hydroxybutyric" should read -- (R)-3-hydroxybutyric --

Column 16,
Line 14, "7.5 x 10e7" should read -- $7.5 \times 10^7$ --
Line 27, "7.5 x 10e7" should read -- $7.5 \times 10^7$ --

Signed and Sealed this

Seventh Day of May, 2002

*Attest:*

JAMES E. ROGAN
*Director of the United States Patent and Trademark Office*

*Attesting Officer*